(12) United States Patent  (10) Patent No.: US 8,472,011 B2
Cronin et al.  (45) Date of Patent: Jun. 25, 2013

(54) MOTION RATE SENSOR (75) Inventors: Nigel J. Cronin, Bath (GB); Adam Guy, Bath (GB)

(73) Assignee: AngioDynamics, Inc., Latham, NY (US)

( * ) Notice: Subject to any disclaimer, the term of this patent is extended or adjusted under 35 U.S.C. 154(b) by 582 days.

(21) Appl. No.: 11/631,456

(22) PCT Filed: Jul. 12, 2005

(86) PCT No.: PCT/EP2005/007553
§ 371 (c)(1),
(2), (4) Date: Nov. 17, 2008

(87) PCT Pub. No.: WO2006/005579
PCT Pub. Date: Jan. 19, 2006

(65) Prior Publication Data
US 2009/0141263 A1  Jun. 4, 2009

(30) Foreign Application Priority Data

Jul. 13, 2004 (GB) .................................. 0415638.6

(51) Int. Cl.
*G01P 3/36* (2006.01)
(52) U.S. Cl.
USPC ........................................ 356/28; 356/28.5
(58) Field of Classification Search
USPC .......................... 356/28, 614, 28.5
See application file for complete search history.

(56) References Cited

U.S. PATENT DOCUMENTS

| 4,730,929 A | 3/1988 | Dausmann |
| 6,275,724 B1 * | 8/2001 | Dickinson et al. ............ 600/424 |
| 2003/0187368 A1 | 10/2003 | Sata et al. |
| 2003/0187369 A1 * | 10/2003 | Lewis et al. .................. 600/587 |

FOREIGN PATENT DOCUMENTS

| GB | 2335744 | 9/1999 |
| JP | 64-054358 | 1/1989 |
| JP | 01-163667 | 6/1989 |
| JP | 2000065600 | 3/2000 |
| JP | 2003307522 | 10/2003 |
| TW | 138941 | 8/1990 |
| TW | 542913 | 7/2003 |

OTHER PUBLICATIONS

English Translation for Notification of Reason for Rejection to Japan Patent Publication No. 64-054358, Dispatched Date May 1, 2012.
Search Report of Patent Application No. 094121352 dated Feb. 7, 2012.

* cited by examiner

*Primary Examiner* — Luke Ratcliffe
(74) *Attorney, Agent, or Firm* — Peter Flora (57) ABSTRACT

A motion rate sensor for detecting the rate of movement of an article, comprising: a housing relative to which, in use, the article moves, a detection unit disposed within the housing, the detection unit including a conversion device adapted for generating detector signals caused by the motion of the article, and processing circuitry adapted for receiving said detector signals and outputting motion signals indicative of the rate of movement of the article. In embodiments, the detector signals are caused by variations in optical or light energy, in magnetic fields or radiation intensity. The variations may be caused by variations on the surface in the article, for example a random or repetitive pattern. An apparatus and method for calibrating the sensor are also disclosed, as are a system and method for determining the speed of motion of an article using the sensor.

13 Claims, 5 Drawing Sheets

| $P_1$ | $P_2$ | $P_3$ | $P_4$ | $P_5$ | $P_6$ | $P_7$ | ... | $P_N$ |
|---|---|---|---|---|---|---|---|---|
| $C_1$ | $C_2$ | $C_3$ | $C_4$ | $C_5$ | $C_6$ | $C_7$ | ... | $C_N$ |
|  | $(C_2-C_1)R$ | $(C_3-C_2)R$ | $(C_4-C_3)R$ | $(C_5-C_4)R$ | $(C_6-C_5)R$ | $(C_7-C_6)R$ | ... | $(C_N-C_{N-1})R$ |

MOTION RATE SENSOR

The present invention relates to electromechanical devices, and in particular to a motion rate sensor.

BACKGROUND OF THE INVENTION

Techniques have long been known for measuring the rate of movement of components in diverse forms of equipment and in various industries. For example, optical techniques for measuring the speed of rotation, of rotating components (such as turntables of phonographic equipment, and rotating parts of automotive engines and other rotary machinery) are well established. Also, translational or linear motion of component can be measured using various gauges and sensor elements or switches. Further, it is known to use optical devices to obtain data indicative of position from a computer mouse.

Difficulties arise when it is desirable to measure with great precision the (possibly relatively slow) rate of linear, axial motion of an elongate article, especially if the article is a relatively delicate or fragile cable or rod. Such problems arise, for example, when it is the rate of movement of a medical implement, or the cable to which it is attached, that is to be accurately monitored/controlled.

The present seeks to overcome the aforementioned problems and provide an improved motion rate sensor.

SUMMARY OF THE INVENTION

The present invention provides a motion sensor for detecting the rate of movement of an article, comprising: a housing relative to which, in use, the article moves, a detection unit disposed within the housing, the detection unit including a conversion device adapted for generating detector signals <-> caused by the motion of the article, and processing circuitry adapted for receiving said detector signals and outputting motion signals indicative of the rate of movement of the article.

Preferably, the housing includes at least one aperture permitting motion of the article relative to the housing.

Preferably, the housing has a configuration whereby, in use, the movement of the article in or near the housing is substantially linear.

Preferably, said at least one aperture includes an entry aperture through which, in use, the article enters the housing, and an exit aperture through which, in use, the article exits the housing, the article preferably moving, in use, in a substantially linear path between said entry aperture and exit aperture.

Preferably, the conversion device comprises of at least one radiation detector adapted for receiving radiation from the article and generating detector signals in dependence on said received radiation.

Preferably, the radiation is optical radiation, the detection unit further includes an optical emitter for emitting the optical radiation, and the radiation detector is disposed so as to receive said optical radiation after reflection from the article. Preferably, the optical emitter is a LED, and preferably wherein the optical emitter and radiation detector comprise an integral device.

Suitably, in the aforementioned embodiments, the article has a plurality of markings or reflective elements disposed on the surface thereof in a repetitive pattern along its length.

Alternatively, in another embodiment, the radiation detector comprises a detector of low-level radioactivity, and the article has a plurality of radioactive elements disposed therein or thereon in a repetitive pattern along its length.

In a further alternative embodiment, the conversion unit includes a magnetic detector, and the article has a plurality of magnetic elements disposed therein or thereon in a repetitive pattern along its length, the magnetic detector being adapted to generate said detector signals when the article, in use, moves past the magnetic detector.

In yet a further In yet In yet a further alternative embodiment, the conversion unit includes one or more rotatable members, such as one or more wheels or balls, adapted to contact the article and be rotated thereby, in use, and an electromechanical device adapted to generate said detector signals in dependence upon the rate of rotation of said rotatable member(s).

According to another aspect of the invention there is provided an apparatus for calibrating the sensor of any of claims 1 to 11, comprising: a runner mounted for linear travel along a slide, the runner including a device for fixedly attaching the article to the runner; a motor, coupled to the runner; a controller, adapted to control the motor to drive the runner, in use, at constant speed along the slide; and a measurement device adapted to measure, in use, signals output by the sensor during the travel of the runner at said constant speed along the slide.

Preferably, the measurement device is adapted to measure count signals, said count signals including a count at the start of a calibration operation and a count at the end of a calibration operation.

Preferably, the measurement device is adapted to calculate a calibration value K (in counts per unit length, for example counts per inch) using $$K = C_c/n_c TV$$

where $C_c$ is the difference between the count at the start of a calibration operation and a count at the end of a calibration operation, T is the polling interval between successive polls of the sensor in seconds, $n_c$ is the number of polling intervals during said travel of the runner along the slide, and V is said constant speed of the runner along the slide in unit length (for example inches) per second.

Preferably, the apparatus further includes a lead screw and a drive nut mounted thereon, the lead screw having a thread of constant pitch; wherein the runner is fixedly attached to the drive nut.

The motor preferably comprises a stepper motor and is arranged to drive the lead screw via cooperating gears.

According to another aspect of the invention there is provided a method of calibrating a sensor, comprising: providing a sensor according to any of claims 1 to 11; providing a calibration apparatus, the calibration apparatus including a runner mounted for linear travel along a slide, the runner including a device for fixedly attaching the article to the runner, a motor, coupled to the runner, and a controller; operating the controller to control the motor to drive the runner at constant speed along the slide; and measuring signals output by the sensor during the travel of the runner at said constant speed along the slide.

Preferably, the measuring step includes measuring a plurality of count signals during the travel of the runner, said count signals including a count at the start of a calibration operation and a count at the end of a calibration operation.

Preferably, the method further includes:
calculating a calibration value K (in counts per unit length, for example counts per inch) using $$K = C_c/n_c TV$$

where $C_c$ is the difference between the count at the start of a calibration operation and a count at the end of a calibration operation, T is the polling interval between successive polls of the sensor in seconds, $n_c$ is the number of polling intervals during said travel of the runner along the slide, and V is said constant speed of the runner along the slide in unit length (for example inches) per second.

According to another aspect of the invention, there is provided a system for determining the speed of motion of an article, comprising: a sensor according to any of claims 1 to 11; a control unit coupled to the sensor for receiving the motion rate signals output thereby; wherein the control unit is configured to poll the sensor, the polling interval between successive polls being of uniform duration; determine a difference value, the difference value being a difference between counts defined by successive motion rate signals; using the determined difference value and a conversion factor R, calculating the speed of motion of the article using R and the difference value.

Preferably, the speed of motion is calculated using $v=(c_i-c_{i-1})R$, where $(c_i-c_{i-1})$ is the difference value. Preferably, the polling interval between successive polls is T, and the conversion factor is determined as $R=1/KT$, where K is a predetermined count conversion constant for the article.

Preferably, the system further includes a display device adapted to display, under the control of the control unit, the calculated speed of motion of the article. Preferably, the display device is adapted to display, under the control of the control unit, a graphical representation of the calculated speed of motion of the article. Preferably, the graphical representation comprises a speedometer-like graphical representation.

According to another aspect of the invention, there is provided a method for determining the speed of motion of an article, comprising: providing a sensor according to any of claims 1 to 11; providing a control unit coupled to the sensor for receiving the motion rate signals output thereby; operating the control unit to poll the sensor, the polling interval between successive polls being of uniform duration; determine a difference value, the difference value being a difference between counts defined by successive motion rate signals; using the determined difference value and a conversion factor R, calculating the speed of motion of the article using R and the difference value.

Preferably, the step of calculating the speed of motion v comprises using $v=(c_i-c_{i-1})R$, where $(c_i-c_{i-1})$ is the difference value. Preferably, the polling interval between successive polls is T, and the conversion factor is determined as $R=1/KT$, where K is a predetermined count conversion constant for the article.

Preferably, the method further includes: providing a display device; and displaying, under the control of the control unit, the calculated speed of motion of the article. Preferably, the display device is adapted to display, under the control of the control unit, a graphical representation of the calculated speed of motion of the article. Preferably, the graphical representation comprises a speedometer-like graphical representation.

BRIEF DESCRIPTION OF THE DRAWINGS

Embodiments of the invention will now be described, by way of example, with reference to the accompanying drawings, in which:

FIG. 1 is a schematic side view of the use of a motion rate sensor, in accordance with an embodiment of the invention, to measure the rate of movement of a cable;

FIG. 2 is (a) a close-up perspective view, and (b) an exploded perspective view of the motion rate sensor of FIG. 1;

FIG. 7 illustrates schematically (a) a time sequence of polling signals, (b) the transmission of signals between sensor 2 and control unit 44, and (c) values obtained in series as a result of the polling.

DETAILED DESCRIPTION OF THE INVENTION

Figures 1, 2A:
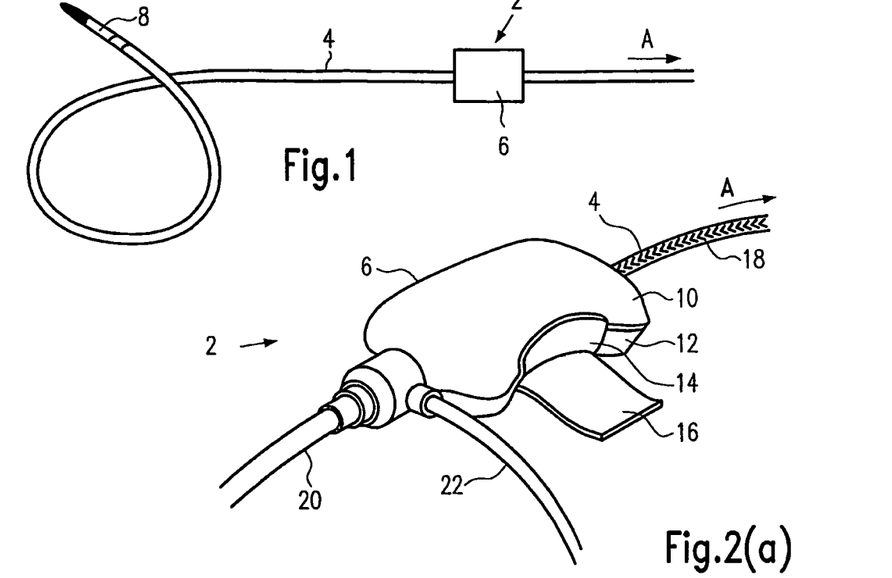

FIG. 1 is a schematic side view depicting the use of a motion rate sensor 2, in accordance with an embodiment of the invention, to measure the rate of movement of a cable 4. In this case, the cable 4 passes through the housing 6 of the sensor 2 as the cable 4 travels in the direction indicated by arrow A; although in alternative embodiments the cable 4 may travel along the side or other surface of the housing 6, or may travel past the housing 6 (with clearance) in the vicinity thereof. That is, any arrangement whereby the motion detector elements (described later) within the housing 6 can perform motion detection may be used.

The motion rate sensor 2 may be used in diverse forms and applications in which the rate of motion of an elongate (flexible or rigid) article is to be measured. Examples include one or more cables used to draw and close curtains or screens in a theatre; and the (typically metal) cables used to open and close a garage door. The motion rate sensor 2 may be used, whether it is the elongate article itself, or some object to which it is to be attached, whose rate of movement is to be measured/controlled. In the example of FIG. 1, a device 8 used in medical procedures on the human body is attached to the end of the cable 4.

FIG. 2(a) shows a close-up perspective view of the motion sensor 2 of FIG. 1. As can be seen, the housing 6 is in two parts—an upper housing 10 and a lower housing 12, suitably fixed together by screws (not shown). Also, a lower clip assembly 14 may be attached (by screws, not shown) to the lower housing 12: the clip assembly 14 is a generally U-shaped cross-section and includes elongate slots (discussed below) enabling a strap 16 to pass therethrough; the strap 16 in turn enables the sensor 2 to be fixedly and stably attached to another object. In the illustrated example, the strap 16 can be used to attach the sensor 2 to the limb of a human body (not shown).

In use, the cable 4 may be pulled in the direction of arrow A, for example by a powered mechanical device such as an electric motor (not shown), by hand, or otherwise. Optionally, the electric motor may be coupled to the same control unit (not shown; discussed further below) that receives signals, as described hereinafter, from the sensor 2 indicative of the rate of movement of the cable 4.

In the illustrated example, the cable 4 comprises coaxial cable having a transparent outer jacket, so that the repetitive pattern of the braided outer conductor of the cable 4 is visible. The detection of the (motion of the) pattern 18 in this embodiment is discussed in further detail below. However, it will be appreciated that the pattern of this braid need not be repetitive, and the jacket need not be transparent. There just needs to be sufficient surface variation on the surface of the cable 4 that is visible by the sensor 2 to allow it find recognizable features and so detect relative position. This variation can be so small that it is not visible to the naked eye. However, in each instance, suitable calibration of the cable (discussed herein below) if preferably employed.

Optionally, in this embodiment, an adaptor 20, attached to the housing 6, may be provided, for initial channeling of a device 8 (see FIG. 1) and the cable 4 in a direction opposite to that indicated by arrow A, and for guiding it into housing 6 during its return travel. In a medical application, an attached tube 22 may be used to extract fluids.

Figures 2B, 2C:
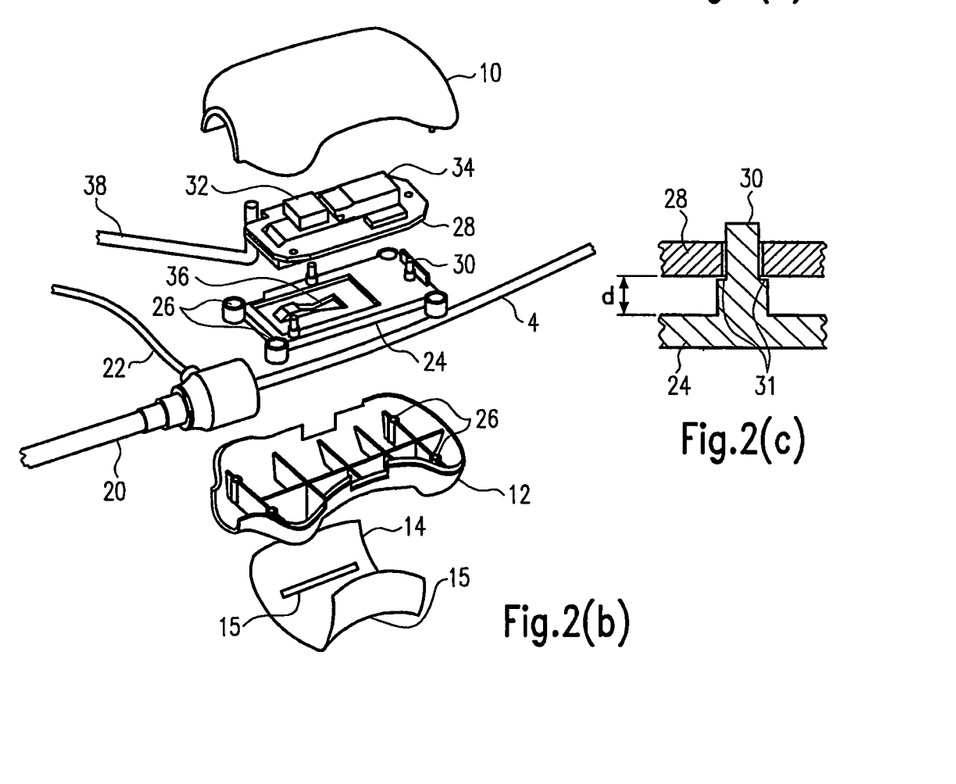

FIG. 2(b) is an exploded perspective view of the motion rate sensor 2 of FIG. 1. The various components of the sensor are shown, including the upper housing 10, lower housing 12, and the clip assembly 14 having two elongate slots 15 for receiving the strap 16 (see FIG. 2(a)).

The cable 4 passes generally parallel to the axis of elongation of the housing 6, and between the lower housing 12 and a base plate 24, the latter of which has screw holes 26 (four of them, in this case) through which fixing screws (not shown) pass from corresponding holes 26 in the lower housing 12 upon assembly.

Mounted above the base plate 24 is a PCB 28 (which will be described further hereinafter), and projection 30 (here: three) are provided on the base plate 24 for this purpose. Referring briefly to the partial cross-section depicted in FIG. 2(c), the projections have two sections of varying diameter, so as to provide shoulders 31 upon which the PCB 28 rests, following assembly.

Referring to FIG. 2(b), mounted on the PCB 28 is a detector device 32 coupled by serial link to a microcontroller 34. The detector device 32 suitably comprises a commercially available optical mouse chip, LED and lens package (ADNK-2620; available from Agilent Technologies); and the microcontroller 34 suitably comprises a Microchip 16 series microcontroller (Part. No. PIC16F627). In use, the LED (not shown) of detector device 32 projects light of a certain wavelength generally downwardly, through optical reader aperture 36 in base plate 24; the light is incident on the (repetitive pattern 18 of the cable 4) and light reflected back off the cable focused by the lens onto a sensor element of the detector device 32. From the variation in received optical signal caused by the movement of the pattern 18 on the cable 4, the detector device 32 generates corresponding electronic signals that are passed to microcontroller 34. In turn, the microcontroller 34 passes signals via cable 38 (conventional RS-232 interface, for example) to a remote control unit, which is described in more detail hereinafter.

It is to be noted that the accuracy of the measurement by the optical motion sensor 2 is largely determined by the degree of play between the cable 4 and the lens. Some form of channel, holder or guide surface, used in a preferred embodiment, to guide the cable 4 in place, under the lens is therefore important. The greater the vertical motion of the cable 4 in this guide, the less accurate the motion rate measurement will be.

It will be appreciated that each of the components 10, 12, 14, 24, 28 of the sensor 2 may be made of conventional materials (e.g. plastics) using well-known moulding techniques. And, when assembled, the sensor 2 may be of compact dimensions and may be in a form similar to a conventional computer mouse.

In an alternative embodiment, magnetic sensing of the rate of motion is used. Here, magnets are placed in or on the cable. Two possible ways of detecting the magnetic fields may be employed. In a first technique, the cable passes through a coil of wire that is built into the housing. As the magnets in the cable pass through coil they generate a current (pulse) that is detected. Either the rate of generation of these pulses, or the magnitude of each pulse, allows calculation of the rate of motion. In a second technique, a Hall probe is used to measure the magnetic field. Once again, the rate of detection of the pulses of magnetic field in conjunction with knowledge of the spacing between magnets, allows the rate of movement to be calculated.

In a further alternative embodiment, reflector elements for sensing of the rate of motion are used. Instead of the Agilent chip described above, a photodiode or phototransistor is used in conjunction with a cable that incorporates more and less reflective sections. Bands alternately having higher and lower reflectivity are used. As each more reflective band passes the sensor, the degree of light detected by the photo detector increases. Once again, knowing the spacing of the bands and the rate of detected pulses allows calculation of the rate of movement.

In a further alternative embodiment, radioactivity detection for sensing of the rate of motion is used. Here, radioactive particles are regularly spaced on the cable. A radioactivity sensor (such as that used in smoke alarms) is used to detect the resulting radiation and provide a pulse as each particle passed the sensor. Once again, knowledge of the spacing between particle and the rate of pulses allows calculation of the speed.

In a further alternative embodiment, resistance measurement for sensing of the rate of motion is used. Alternatively, the article has regions of varying dielectric strength and passes through the plates of a capacitor. Alternatively, the article has regions of varying thickness and a proximity measurement is made. Alternatively, the article has regions of opacity and transparency, with a source and detector facing each other with the article passing between the two. (This opacity and transparency could be to visible light, any electromagnetic signal, radioactivity, magnetic field, or electric field).

All of these alternative embodiments may be used in conjunction with the example provided above that employs the Agilent LED/optical sensor chip, to provide additional information on the position of the cable. For example, a small reflective band, or magnetic particle may be placed near the end of the cable. If the housing incorporates the relevant detection device, when the cable reaches this position, a single pulse will be delivered to the system to signal that the end of the cable is approaching.

Figure 3:
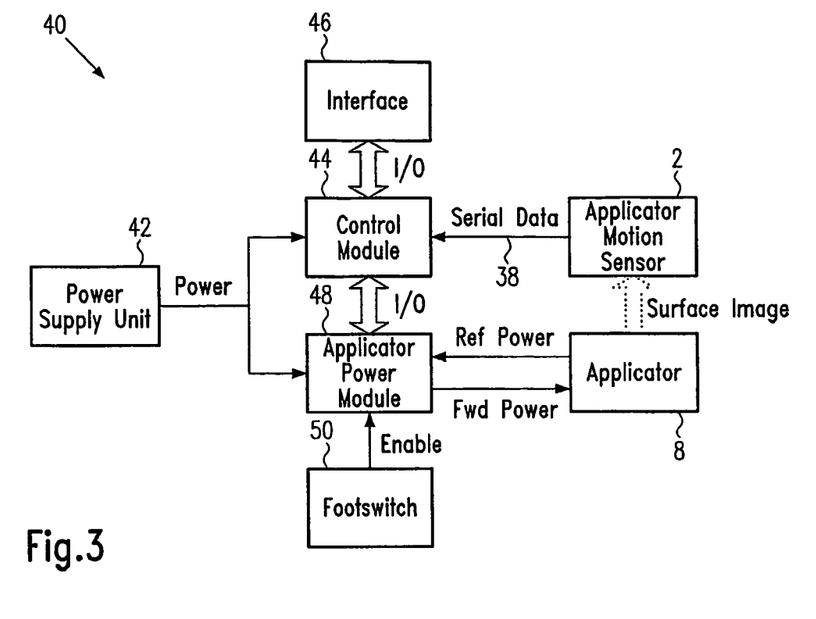
FIG. 3 schematically illustrates a system, in accordance with one aspect of the invention, for performing the controlled movement of an article, using the sensor of FIGS. 1 and 2.

FIG. 3 schematically illustrates a system, in accordance with one aspect of the invention, for performing the controlled movement of an article, using the above-described motion rate sensor 2. The system (generally designated 40) includes a PSU 42, a control module 44 and a user interface (UI) 46. As mentioned, the motion rate sensor 2 is coupled to the control module 44 by serial link (38). As is conventional, the UI 46 may present graphical, audible or graphical and audible information (not shown) to the user via well-known display and/or speaker technology, under the control of the control module 44.

As mentioned with reference to FIG. 1, in the illustrated embodiment, the cable 4 may be attached to a medical device 8 (treatment applicator) whose rate of motion is to be monitored/controlled. Optionally, therefore, with reference to FIG. 3, the system 40 may include the medical device 8 (applicator), a power module 48 able to adjust power supplied to the medical device 8 in dependence upon the motion rate data supplied to it by the control-module, and a user-operable footswitch 50 enabling the user to switch the power on or off.

Figure 4:
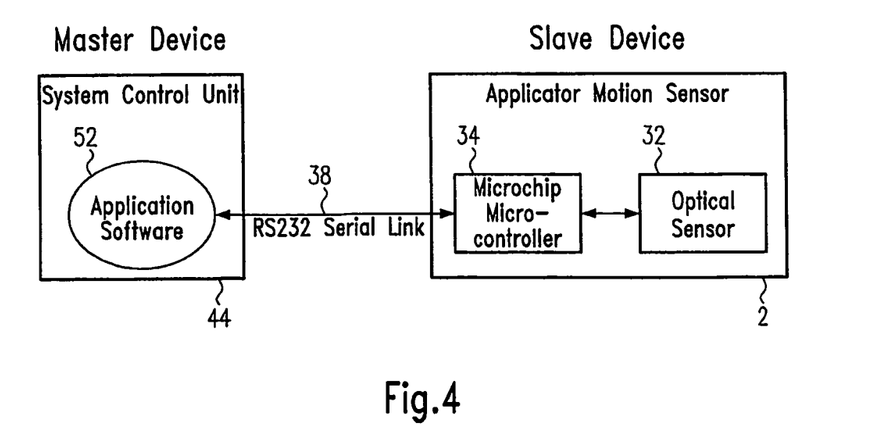
FIG. 4 illustrates schematically in more detail the communication between the motion rate sensor and the control module in the system of FIG. 3.

FIG. 4 illustrates schematically in more detail the communication between the motion rate sensor 2 and the control module 44 in FIG. 3. When the sensor 2 is connected to the system 40 to provide feedback to the user, the data is suitably transferred by a standard protocol, such as RS232. The sensor 2 is connected to the control unit 44 of the system 40, and the comms port (not shown) of the system 40 regularly polled by the system's software 52 to extract the data on the sensor's position. From the position data, the rate of motion can be derived. However, it will be appreciated that other protocols (and cables) may be used instead of RS232, e.g. RS485, RS422, I2C, USB, GP1 B, parallel or other protocol. The rate of polling the sensor 2 to determine the motion rate is determined by the degree of resolution of the sensor and the desired motion rate (as discussed hereinafter).

Figure 5:
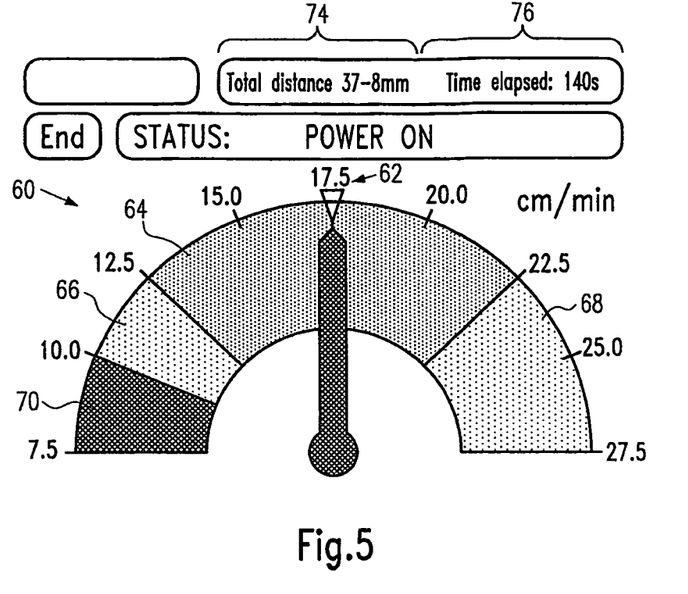
FIG. 5 illustrates an example of a user interface displayed to the user by the system of FIG. 3.

FIG. 5 depicts an example of a UI view displayed to the user by the system 40 of FIG. 3. As can be seen, there is displayed graphically a "speedometer-type" meter 60. The meter 60, as well as displaying specific values, including the current value 62, also has several coloured zones, including a green zone 64, two orange zones 66, 68, and a red zone 70. Thus, the user has visual feedback as to whether the rate of motion of the article 4 sensed by the sensor 2 (see FIG. 1)

(i) is at an optimal value (pointer 71 pointing straight up),
(ii) is at an acceptable value (pointer 72 within green zone 64),
(iii) is at a somewhat unacceptable value (pointer 72 within orange zones 66, 68), or
(iv) is at a highly unacceptable value (pointer 72 within red zone 70).

Alternatively or additionally, audible information may be emitted by the UI 46, corresponding to the different aforementioned zones, i.e. with green→orange→red zones corresponding to increasingly higher tone (sonic frequency), or corresponding to sonic pulses ("beeps") being emitted at different (increasing green→orange→red) rate for different zones.

Additionally, the UI 46 may be caused by software to display (at 74) the total distance traveled by the article (cable) 4, and/or (at 76) the total elapsed time during the travel of the article.

Figure 6:
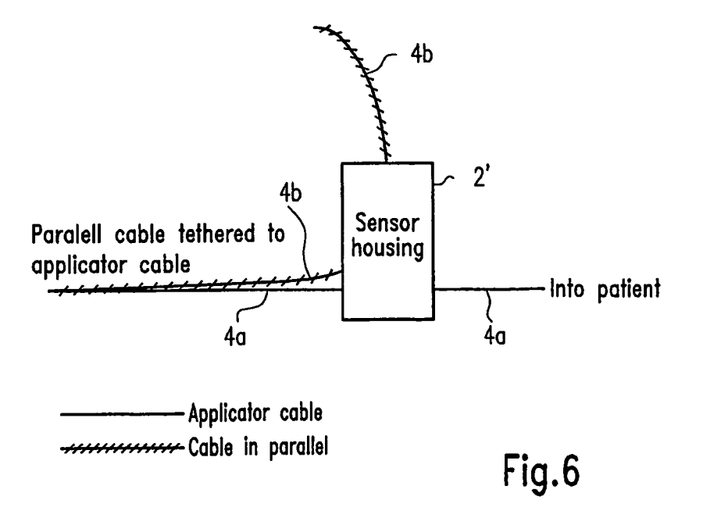
FIG. 6 shows an alternative embodiment of the motion rate sensor—in the case where two cables are used.

FIG. 6 shows an alternative embodiment of the motion rate sensor 2'—in the case where two cables are used. The construction is the same as the embodiment of FIGS. 1 and 2, except as follows. Here, two tethered cables 4a, 4b, that run in parallel for most of their length, separate first before passing through the sensor 2'. The applicator cable 4a (e.g. supplying power to a treatment device (not shown)) passes through the sensor 2' transversely. The parallel cable 4b, having detectable markings thereon, passes through the sensor 2', has its marking detected by the detector device (see FIG. 2), and exits the sensor 2' longitudinally.

Although the motion rate sensor has been described above in relation to a simple medical application, it will be appreciated by persons skilled in the art that the invention may be employed in any situation in which the rate of movement of an article is to be measured and/or controlled. Examples include all sorts of cable operated devices, equipment and machinery. The aforementioned (automatic) cable operated curtains and garage doors are typical examples. The motion of moving rods, cables and threads in manufacturing environments (e.g. the weaving industry) may also be measured using techniques according to the invention.

Figure 7A:
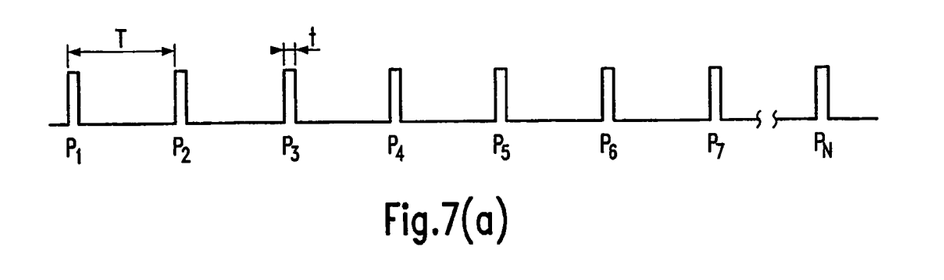
Figure 7B:
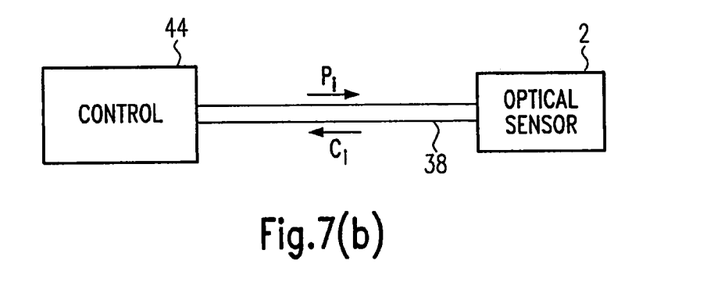

FIG. 7(a) illustrates schematically a time sequence of polling signals issued by the control unit 44 down serial line 38 to the sensor 2 (see FIG. 7(b)). As can be seen, the polling (here illustrated schematically as a single pulse of duration t) occurs at regular intervals with a polling interval T. The polling pulses are labeled $p_{-1}, p_2, p_3, p_N$.

FIG. 7(b) shows the transmission of signals between sensor 2 and control unit 44, such that, in response to pulse p, a count c, is returned by the sensor 2. Suitably, the count q is defined by a multi-bit digital signal sent down the serial line 38. Before use, the sensor 2 is reset. During use the sensor 2 need not be re-set. In one embodiment, the polling interval T is 0.2 seconds.

Figure 7C:
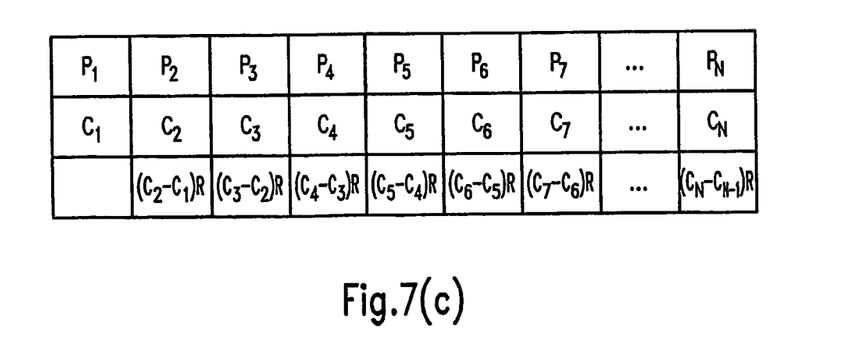

FIG. 7(c) shows values obtained in series as a result of the polling. In the first row is the sequence of polling pulses pi, and in the second are the counts Cj that are returned in response to the respective polling pulse. In order to convert these values q to values representing motion, the counts value from the time the sensor 2 was last polled is subtracted from the present counts value. This gives the number of counts the cable 4 has moved relative to the sensor 2 during the polling interval T. The number of counts is then divided (or multiplied) by a constant (counts-per-inch) to give the actual distance moved in the units required by the system (control unit 44). It is then divided by the time interval to give the rate of motion. Thus, the speed, i.e. the average speed over the last polling interval T, for a given polling pulse i is given in the third row in FIG. 7(c): speed $V=(C_i-C_{i-1})R$, where R is a conversion factor. If it has been previously determined, e.g. using suitable calibration techniques, discussed hereinafter, that the number of counts-per-inch for the cable is K, then $R=1/(KT)$. The speed v (in inches/second) is calculated by the control unit 44 using this relation, and using a stored value for R.

In the embodiment described, K is around 460 counts per inch, and T=0.2 s. So, for example, if the cable moves 10 counts in 0.2 seconds, the rate is (10/460)/0.2=0.1087 inches per second. As mentioned, this gives a value of speed v every 0.2 seconds. This is not an instantaneous speed, but a value that is the average speed over the previous 0.2 s.

The polling interval T is also important in determining accuracy. It is related to the speed of motion of the cable 4. If T is so short that very few counts have been accumulated between polls, then discrimination errors will occur, as measured rate will appear to be one of several discrete values. The polling interval may need (depending on whether such errors are important in the application) to be chosen such that sufficient counts are read by the sensor 2 between polling pulses to make such errors unrecognizable. A faster cable movement will allow a higher rate of polling (and therefore shorter T). A slower one will require a lower rate of polling. On the other hand, if T is made too long, then the rate recorded will start to noticeably lag behind the actual movement, as it is effectively an average over the polling interval T. In the currently preferred embodiment, the lowest effective value of the polling interval T, with a pullback rate (i.e. rate of movement of cable 4) of 10 cm/min or greater, is around 0.2 s.

In an alternative embodiment, if an average speed is required, but without large T and hence long intervals between speed updates, then shorter polling intervals T can be used in conjunction with a rolling average calculation: here, control unit 44 computes the mean value of the preceding n speed results. This is has the advantage that the displayed or measured speed will vary more smoothly over time. The shorter the polling interval T, the less jerky the response. The greater n is, the more damped the response. This produces advantages in the display of speed to the user, particularly when the aforementioned "speedometer-type" display of cable speed (see FIG. 5) is employed. The number n of past speed values that are averaged may be any suitable number, e.g. from a few to a few tens of values. Typically, n<=32. In a preferred embodiment, n is 16 (i.e. providing a speed averaged over 16×0.2=3.2 s). However, it will be appreciated that, depending on the application, the upper limit on n may be several tens, several hundreds or more. The upper limit may have any suitable value reasonably applicable to the parameters of the apparatus being used.

The number of counts measured per unit distance will vary slightly with withdrawal speed. A higher withdrawal speed will result in a slightly lower number of counts per unit distance. In order to assess the appropriate calibration factor to use in the system to convert the number of counts to distance and hence speed, a device has been designed and built to accurately withdraw the cable through the sensor at a known fixed rate. This therefore means that the calibration factor for any particular withdrawal rate can be accurately assessed.

Figure 8:
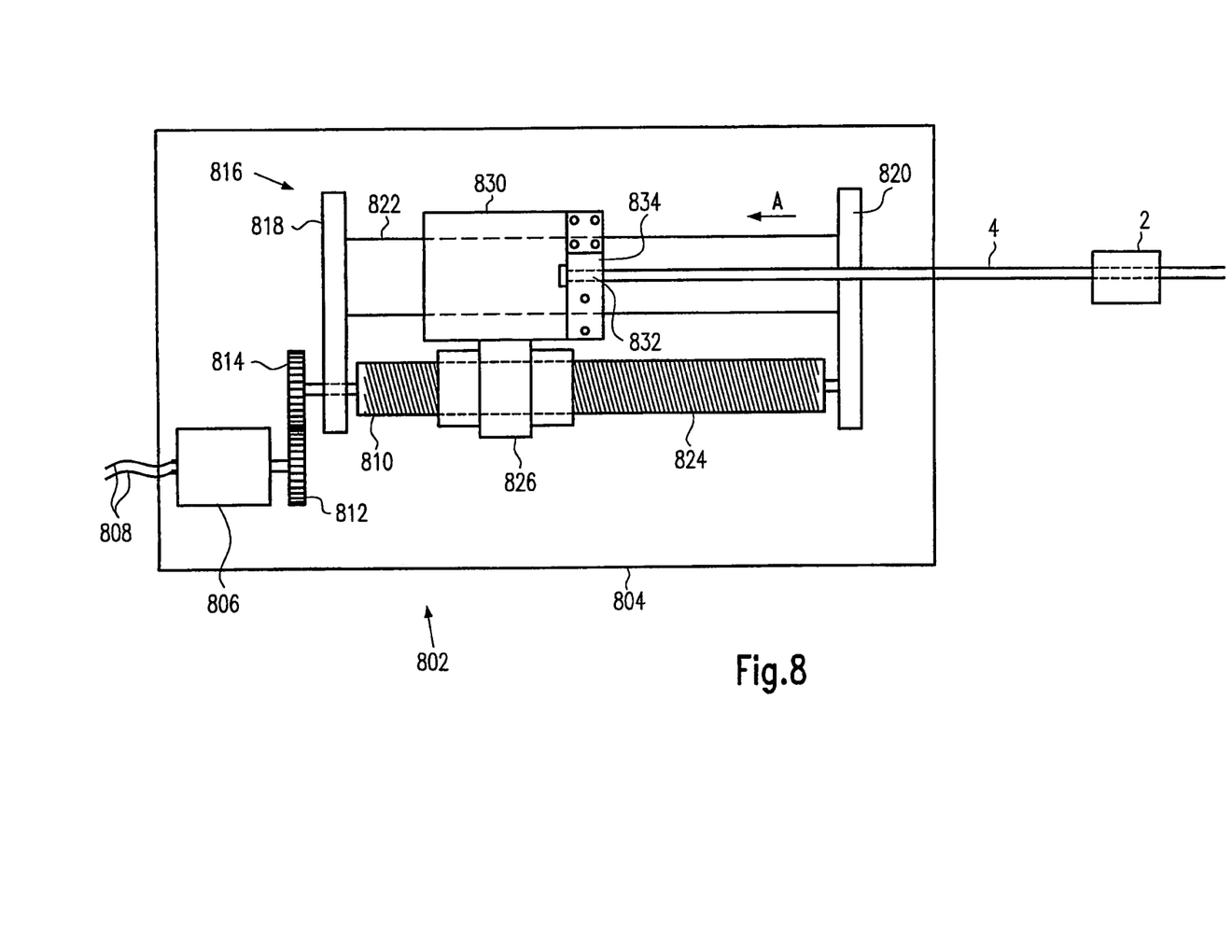
FIG. 8 illustrates a plan view of a calibration apparatus that may be employed according to embodiments of the invention.

FIG. 8 illustrates a plan view of a calibration apparatus 802 that may be employed according to embodiments of one aspect of the invention. The calibration apparatus 802 includes a rigid base 804 onto which various components, described hereinafter, are fixedly mounted. These include a stepper motor 806 is coupled to a computer (not shown) via cables 808, and driven under the control of the computer, as is well known in the art. The stepper motor 806 transmits rotary motion to a lead screw 810 via co-operating gears 812, 814, of the spur gear type. The lead screw 810 is mounted for rotation on a rigid frame 816 that includes endplates 818, 820, and slide 822.

The lead screw 810 is provided with an external helical thread 824 of constant, known pitch; and a drive nut 826 is provided on the lead screw 810 and has a co-operating internal thread (not shown). The drive nut 826 is in turn rigidly attached to a runner 830 mounted on the slide 822. The runner 830 and slide 822 preferably have co-operating guide elements and/or wheels/bearings (not shown) so as to facilitate low-friction sliding of the runner 830 along the slide 822. Suitably, the length of travel of the runner 830 on the slide 822 is of the order of 0.5-1.0 m.

A sensor 2 to be calibrated is provided a suitable distance (e.g. 1-2 m) from end plate 820 of the frame 816 and is fixed relative thereto, e.g. by clamping or screws (not shown). The cable 4 passes through the sensor 2 and its end 832 is clamped (e.g. by suitable plates and screws) by a clamping element 834 on the runner 830.

Calibration (for determining the counts-per-inch K of the cable 4 using the sensor 2) consists of the following. The sensor 2 is set up for issuing the accumulated count value c, after successive polling intervals T. The drive nut 826 is placed at the end of its travel adjacent the end plate 820 of frame 816. With the cable 4 passing through the sensor 2, and with any excessive slack in the cable 4 removed, the stepper motor 806 is powered up and driven at constant rotational speed by the control computer (not shown); thus, the runner 830 is driven along the slide by drive nut 826 at a known constant linear speed V (inch/s).

A calibration operation may comprise measuring the count at the end of the travel of the runner 830 and that at the start of the travel. More preferably, a calibration operation comprises measuring the count at least at a "start of calibration", i.e. a predetermined time after the runner has started its motion on the slide, and has clearly reached the constant speed, and measuring the count at the "end point of the calibration", i.e. a predetermined time before the runner has ended its motion. This has the benefit of eliminating distortion due to acceleration and deceleration periods.

If the difference between the count at the end of the travel of the runner 830 and that at the start of the travel is C0, and the number of polling intervals T is n0, than the counts-per-inch K can be obtained from $$V=(C_c K)/n_c T$$

or $K=C_c/n_c TV$

This is one calibration operation. It will be appreciated that, for one sensor-cable combination, this operation may be repeated several or many times, and the obtained values K averaged.

Once the value K is known, this can be used to measure motion rate, as discussed above in relation to FIG. 7. It will be appreciated by persons skilled in the art that, once a value for K has been established, one or more of the other parameters in the relationship $K=C_c/n_c TV$ can thereafter be obtained.

It will be immediately apparent that, although inches have been used as units in certain embodiments, other units may be used. That is, instead of expressing K in counts-per-inch, this may be counts-per-mm, per-cm, per-m, or counts per custom unit; and instead of expressing V in inches/second, this may be in mm/s, cm/s, m/s; and so on.

The invention claimed is:

1. A system comprising:
a cable attached at a first end to a medical treatment applicator and at a second end to a power module adapted to adjust power supplied to the treatment applicator, and
a motion rate sensor for detecting a rate of substantially linear movement of the cable, the motion rate sensor comprising:
a housing relative to which, in use, the cable moves,
a detection unit disposed within the housing, the detection unit including
a conversion device comprising at least one radiation detector adapted for receiving radiation from the cable, the conversion device being adapted for generating detector signals caused by the motion of the cable in dependence on said received radiation, and
processing circuitry adapted for receiving said detector signals and outputting motion signals indicative of the rate of movement of the cable.

2. The system of claim 1, wherein the housing includes at least one aperture permitting motion of the cable relative to the housing.

3. The system of claim 2, wherein the housing has a configuration whereby, in use, the movement of the cable in or near the housing is substantially linear.

4. The system of claim 2, wherein said at least one aperture includes an entry aperture through which, in use, the cable enters the housing, and an exit aperture through which, in use, the cable exits the housing, the cable moving, in use, in a substantially linear path between said entry aperture and exit aperture.

5. The system of claim 1, wherein the radiation is optical radiation, the detection unit further includes an optical emitter for emitting the optical radiation, and the radiation detector is disposed so as to receive said optical radiation after reflection from the cable.

6. The system of claim 5, wherein the optical emitter is a LED.

7. The system of claim 1, wherein the cable has a plurality of markings or reflective elements disposed on the surface thereof in a repetitive pattern along its length.

8. The system of claim 1, wherein the radiation detector comprises a detector of low-level radioactivity, and the cable has a plurality of radioactive elements disposed therein or thereon in a repetitive pattern along its length.

9. The system of claim 1, wherein the conversion unit includes a magnetic detector, and the cable has a plurality of magnetic elements disposed therein or thereon in a repetitive pattern along its length, the magnetic detector being adapted to generate said detector signals when the cable, in use, moves past the magnetic detector.

10. The system of claim 1, comprising a control unit coupled to the sensor for receiving motion rate signals output thereby and a display device adapted to display, under the control of the control unit, the calculated speed of motion of the cable.

11. The system of claim 10, wherein the display device is adapted to display, under the control of the control unit, a graphical representation of the calculated speed of motion of the cable.

12. The system of claim 11, wherein said graphical representation comprises a speedometer-like graphical representation.

13. The system claim 5, wherein the optical emitter and radiation detector comprise an integral device.

\* \* \* \* \*